United States Patent
Nishiguchi

(10) Patent No.: US 9,174,910 B2
(45) Date of Patent: *Nov. 3, 2015

(54) METHOD FOR PRODUCING ACRYLIC ACID WITH A FIXED-BED MULTITUBULAR REACTOR

(71) Applicant: Nippon Shokubai Co., Ltd., Osaka (JP)

(72) Inventor: Toshiya Nishiguchi, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/383,705

(22) PCT Filed: Mar. 28, 2013

(86) PCT No.: PCT/JP2013/059279
§ 371 (c)(1),
(2) Date: Sep. 8, 2014

(87) PCT Pub. No.: WO2013/147032
PCT Pub. Date: Oct. 3, 2013

(65) Prior Publication Data
US 2015/0057464 A1   Feb. 26, 2015

(30) Foreign Application Priority Data

Mar. 29, 2012 (JP) ................ 2012-077490

(51) Int. Cl.
| | | |
|---|---|---|
| C07C 51/16 | (2006.01) | |
| C07C 45/00 | (2006.01) | |
| C07C 45/35 | (2006.01) | |
| B01J 27/192 | (2006.01) | |
| C07C 51/235 | (2006.01) | |
| B01J 23/889 | (2006.01) | |
| B01J 23/00 | (2006.01) | |
| B01J 23/28 | (2006.01) | |
| B01J 23/888 | (2006.01) | |
| B01J 27/199 | (2006.01) | |
| C07C 51/25 | (2006.01) | |

(52) U.S. Cl.
CPC ............ *C07C 51/235* (2013.01); *B01J 23/002* (2013.01); *B01J 23/28* (2013.01); *B01J 23/8885* (2013.01); *B01J 23/8892* (2013.01); *B01J 27/199* (2013.01); *C07C 51/252* (2013.01)

(58) Field of Classification Search
None
See application file for complete search history.

(56) References Cited

U.S. PATENT DOCUMENTS

| | | |
|---|---|---|
| 5,739,392 A | 4/1998 | Tanimoto et al. |
| 2003/0006026 A1 | 1/2003 | Matsumoto et al. |
| 2003/0125580 A1 | 7/2003 | Yunoki |
| 2006/0211885 A1 | 9/2006 | Yoo et al. |
| 2007/0003460 A1 | 1/2007 | Matsumoto et al. |
| 2009/0247787 A1 | 10/2009 | Yoo et al. |
| 2015/0045581 A1* | 2/2015 | Kawano et al. ............... 562/546 |

FOREIGN PATENT DOCUMENTS

| | | |
|---|---|---|
| JP | 7-10802 | 1/1995 |
| JP | 8-206504 | 8/1996 |
| JP | 2003-1094 | 1/2003 |
| JP | 2003-89671 | 3/2003 |
| JP | 2003-171340 | 6/2003 |
| JP | 2004-244383 | 9/2004 |
| JP | 2005-120079 | 5/2005 |
| JP | 2006-7205 | 1/2006 |
| JP | 2008-535784 | 9/2008 |

OTHER PUBLICATIONS

International Search Report issued Jul. 2, 2013 in International (PCT) Application No. PCT/JP2013/059279.

\* cited by examiner

*Primary Examiner* — Yevegeny Valenrod
(74) *Attorney, Agent, or Firm* — Wenderoth, Lind & Ponack, LLP.

(57) ABSTRACT

This invention provides a method for producing acrylic acid by catalytic gas-phase oxidation, which method makes it possible to carry out a continuous operation steadily for a long period of time while a high yield is maintained.

This method is characterized by comprising filling each of reaction tubes of a fixed-bed multitubular reactor with at least two species of catalysts each of which essentially comprises, as catalytically active components, oxide of molybdenum and oxide of vanadium and/or composite oxide of the same, said at least two species of catalysts being different in the ratio of D1/D2, D1 denoting the proportion of the total pore volume of pores whose pore diameter falls within the range of at least 0.03 μm and less than 0.4 μm to the total pore volume of the whole pores, and D2 denoting the proportion of the total pore volume of pores whose pore diameter fails within the range of at least 0.4 μm and at most 5 μm to the total pore volume of the whole pores, in such a manner that at least two reaction zones are formed axially in each of the reaction tubes.

11 Claims, No Drawings

METHOD FOR PRODUCING ACRYLIC ACID WITH A FIXED-BED MULTITUBULAR REACTOR

TECHNICAL FIELD

This invention relates to a method for producing acrylic acid by catalytic gas-phase oxidation reaction of acrolein with a fixed-bed multitubular reactor. In more detail, this invention relates to a method for producing acrylic acid by catalytic gas-phase oxidation reaction of acrolein with a fixed-bed multitubular reactor, reaction tube of which is filled with two or more catalyst layers.

BACKGROUND ART

Industrial-scale catalytic gas phase oxidation reaction generally uses a fixed-bed reactor in which a starting compound-containing gas is made to pass through a reaction tube filled with catalyst and is thus allowed, to react. In particular for the production of (meth)acrolein and (meth)acrylic acid by catalytic gas-phase oxidation reaction of propylene, propane, isobutylene, etc., as a raw material compound, there has widely been employed a catalytic gas-phase oxidation reaction with a fixed bed multitubular reactor which is filled with solid particulate heterogeneous catalyst. Solid particulate heterogeneous catalyst which is to be used for this purpose generally includes a molded catalyst (unsupported catalyst) which is composed of active ingredients which have been molded into a specific geometric shape and a supported catalyst which is composed of a carrier material which has a geometric shape like that of molded catalyst and which has been coated with active ingredients (Patent Document 1).

Most popular for producing acrylic acid with a fixed-bed multitubular reactor which is filled with solid particulate heterogeneous catalyst is a method of two-step catalytic gas-phase oxidation by which acrolein is mainly obtained by catalytic gas-phase oxidation of propylene, and, then, acrylic acid is obtained by catalytic gas-phase oxidation of thus obtained acrolein. Also for the second step reaction of producing acrylic acid by the oxidation of acrolein, there have been proposed various methods for producing acrylic acid with a high yield. Most of such proposals relate to molybdenum-vanadium catalysts each of which mainly comprises molybdenum and vanadium which are used in the above-mentioned reaction, in detail to the composition, shape, physical properties of the catalysts and how to produce the same (Patent Documents 2, 3, and the like). There have also been made some proposals which relate to how to fill reaction tubes of a fixed-bed multitubular reactor with catalyst (Patent Documents 4, 5 and 6).

CITATION LIST

Patent Literature Documents

Patent Document 1: Japanese Patent Application KOKAI Publication No. 2003-1094
Patent Document 2: Japanese Patent Application KOKAI Publication No. 2006-7205
Patent Document 3: Japanese Patent Application KOKAI Publication No. H8-206504
Patent Document 4: Japanese Patent Application KOKAI Publication No. 2004-244383
Patent Document 5: Japanese Patent Application KOKAI Publication No. H7-10802
Patent Document 6: Japanese PCT Application KOHYO Publication No. 2008-535784

SUMMARY OF INVENTION

Technical Problem

When worked on industrial scale, however, the above-mentioned publicly known methods still leave room for improvement in respect to the yield, catalyst life, etc., of acrylic acid of interest.

The problem to be solved by this invention is how to provide a method for producing acrylic acid, by which a continuous operation can be carried out steadily for a long period of time in gas-phase catalytic oxidation of op lone while a high yield is maintained.

Solution to Problem

In order to solve the above-mentioned problem, the inventors of this invention made a detailed study about catalysts which might be usable for catalytic gas phase oxidation and on how to fill reaction tubes of a fixed-bed multitubular reactor with catalyst. As a result, they have found out that, when reaction tubes of a fixed-bed multitubular reactor are filled with at least two species of catalysts which are different in pore size distribution, and each of which comprises molybdenum and vanadium as essential components, the desired products are favorably affected with regard to their performance such as yield, catalyst life, etc. This invention, thus provides a method for producing acrylic acid stably for a long period of time white a high yield is maintained, which method comprises filling each of reaction tubes of a fixed-bed multitubular reactor with at least two species of catalysts each of which comprises, as catalytically active components, oxide of molybdenum and oxide of vanadium and/or composite oxide of the same, said at least two species of catalysts being different in the ratio of D1/D2, D1 denoting the proportion of the total pore volume of pores whose pore diameter falls within the range of at least 0.03 μm and less than 0.4 μm to the total pore volume of the whole pores, and D2 denoting the proportion of the total pore volume of pores whose pore diameter falls within the range of at least 0.4 μm and at most 5 μm to the total pore volume of the whole pores, in such a manner that at least two reaction zones are formed axially in each of the reaction tubes.

Advantageous Effects of Invention

When reaction tubes of a fixed-bed multitubular reactor are filled with catalyst in the above-mentioned manner, this invention produces effects as follows:
(1) Acrylic acid is obtained with a high yield:
(2) Catalyst can be used stably for a long period of time; and
(3) Acrylic acid is obtained stably with a high yield from reaction under heavy load conditions such as a high concentration of raw material or a high space velocity.

DESCRIPTION OF EMBODIMENTS

In the following, this invention is explained in more detail. The scope of this invention is, however, not limited by the following explanation, but may be changed appropriately when this invention is to be worked, so long as the essence of this invention is not adversely influenced.

This invention relates to a method for producing acrylic acid by the catalytic gas-phase oxidation of acrolein with molecular oxygen by a fixed-bed multitubular reactor, which method comprises filling each of reaction tubes of a fixed-bed multitubular reactor with at least two species of catalysts each, of which essentially comprises, as catalytically active components, oxide of molybdenum and oxide of vanadium and/or composite oxide of the same, said at least, two species of catalysts being different in the ratio of D1/D2, D1 denoting the proportion of the total pore volume of pores whose pore diameter fails within the range of at least 0.03 μm and less than 0.4 μm to the total pore volume of the whole pores, and D2 denoting the proportion of the total pore volume of pores whose pore diameter falls within the range of at least 0.4 μm and at most 5 μm to the total pore volume of the whole pores, in such a manner that at least two reaction zones are formed axially in each of the reaction tubes.

No particular limitation is to be placed on fixed-bed multitubular reactor for this invention. Any type that has been generally employed for catalytic gas-phase oxidation is usable so long as the same is filled with catalyst in the above-mentioned manner. For instance, those which are conventionally known such as single reactor and tandem reactor can be suitably employed.

Gas-phase oxidation catalyst which is usable for this invention essentially comprises molybdenum and vanadium, and suitably comprises a catalytically active component of formula (1) as follows:

$$Mo_{12}V_aW_bA_cB_dC_eD_fO_x \quad (1)$$

wherein Mo is molybdenum; V is vanadium; W is tungsten; A is at least one species of element selected from the group consisting of chromium, manganese, iron, cobalt, nickel, copper, zinc and bismuth; B is at least one species of element selected from the group consisting of antimony, niobium, tin, tellurium and phosphorus; C is at least one species of element selected from the group consisting of silicon, aluminum, titanium, cerium and zirconium; D is at least one species of element selected from the group consisting of alkali metals and alkaline earth metals; and O is oxygen; and a, h, c, d, e, f and x each denote number of atoms of V, W, A, B, C, D and O, and $0<a\leq14$, $0\leq b\leq12$, $0\leq c\leq30$, $0\leq d\leq6$, $0\leq e\leq50$, and $0\leq f\leq6$, and x is a value determined by the state of oxidation of each of the elements. Preferable in the above-mentioned formula (1) are those wherein A is at least one species of element, selected from the group consisting of iron, cobalt, nickel and copper; B is at least one species of element selected, from the group consisting of antimony and niobium; and $2\leq a\leq10$, $0.2\leq b\leq6$, $0.1\leq c\leq10$ and $0.1\leq d\leq4$ is preferred.

Preferable as a catalyst of this invention is a supported catalyst in which the above-mentioned catalytically active components are supported on any desired inert carrier which has a specific shape.

Examples of inert carrier usable include alumina, silica, silica-alumina, titania, magnesia, steatite, cordierite, silica-magnesia, silicon carbide, silicon nitride, zeolite, and the like, among which alumina, silica, silica-alumina, steatite and cordierite are preferable. The inert carrier may have any publicly known shape including spherical, cylindrical or ring shape without any particular limitation. The amount of catalytically active components supported on the supported catalyst preferably ranges from 10 to 300% by mass, more desirably from 20 to 200% by mass, although there is no particular limitation on the same.

Catalysts of this invention may be prepared by methods which are generally employed for the preparation of catalysts of this type, e.g., by a method as follows.

There is no particular limitation to be placed on starting materials which are usable for the catalytically active components of this invention. For example, oxides, hydroxides or salts (ammonium salts, nitrates, carbonates, sulfates or organic acid salts) which contain each of the component elements, aqueous solution or sol of the same, compounds which contain two or more of the component elements, or combination of the same are usable.

Firstly, starting material for the catalytically active component as mentioned above is dissolved or suspended, for instance in water, to make an aqueous solution or an aqueous slurry (hereinafter sometimes referred to as "starting material mixture liquid").

Starting material mixture liquid as mentioned above can be prepared by any method that is usually employed for the preparation of catalyst of this kind. For example, one may prepare aqueous solutions or aqueous slurries which respectively contain starting materials for the above-mentioned catalytically active components, and mix the same with one another. Otherwise, one may prepare two or more aqueous solutions or aqueous slurries for each of starting materials for the catalytically active components, and divide the aqueous solutions or slurries and mix the resultant divisions with one another. No limitation is to be placed on the condition of mixing (order of mixing, temperature, pressure, pH, etc) of starting materials for the catalytically active components.

Thus obtained starting material mixture liquid is used in a conventional supporting process, in the form of a liquid as the same has been heat-treated. Otherwise, a catalytic precursor in the form of a solid may be prepared from said starting material mixture liquid, through a drying process (primary drying process) by such a method as heating or pressure reduction, for use in supporting process which is mentioned later.

In order that a catalytic precursor may be prepared by heat drying in the primary drying process, a starting material mixture liquid may be either dried by evaporation to make a cake-like catalytic precursor, or dried by a spray dryer or a drum dryer to make a powdery catalytic precursor, or heated in an air stream with a box-type dryer, a tunnel dryer or the like to make a block or flake catalytic precursor. Otherwise, a cake-like solid, which has been prepared by the drying of a starting material mixture liquid by evaporation may be further heated in an air stream with a box-type dryer, a tunnel dryer or the like to make a block or flake catalytic precursor.

In order that a solid catalytic precursor may be prepared by drying under reduced pressure in the primary drying process, a vacuum dryer for example may be used to obtain, a block or powdery catalytic precursor.

Furthermore, a solid catalytic precursor which has been prepared by the above-mentioned primary drying process may be uninterruptedly calcined to make a catalytic precursor.

Thus obtained catalytic precursor may be pulverized or classified where necessary, to make a powdery catalytic precursor with a moderate particle size. In that case, there is no particular limitation on the particle size of the powder of catalytic precursor. Nevertheless, in order that good supportability may be achieved for the supporting process which is mentioned later, the particle size is preferably 500 μm or less, more desirably 200 μm or less.

There is no limitation on how to make catalytically active components supported on an inert carrier. There may be employed a method which is disclosed in Japanese Patent Application KOKOKU Publication No. S49-11371 wherein the above-mentioned starting material mixture liquid, is heated with stirring so as to be dried by evaporation to adhere to an inert carrier which has a specific shape, or a method which is disclosed in Japanese Patent Application KOKAI Publication Nos. S64-85139, H8-299797 or 2004-136267 wherein the above-mentioned powdery catalytic precursor is made to be supported on an inert carrier which has a specific shape.

In the supporting process wherein the above-mentioned catalytically active components are made to be supported on an inert carrier, adjuvant or binder may be used so that supportability may be improved. Examples of the same include organic compounds such as ethylene glycol, glycerin, propionic acid, maleic acid, benzyl alcohol, propyl alcohol, butyl alcohol and phenols; and water, nitric acid, ammonium nitrate, ammonium carbonate and urea.

In order to improve its mechanical strength, the catalyst of this invention ma contain glass fiber or ceramic fiber which is generally known as a reinforcement, or fiber made from inorganic material such as silica, alumina, silicon carbide and silicon nitride. Inorganic fiber as mentioned above may be added by any method without particular limitation, as long as the inorganic fiber is uniformly dispersed in the catalyst. For example, inorganic fiber may be added to a starting material mixture liquid, or inorganic fiber may be mixed with a solid catalytic precursor in the supporting process.

Supported body which has been obtained by the above-mentioned supporting process is sent to the calcination process after having passed through the secondary drying process where necessary.

In the secondary drying process, supported body is dried by heating in an atmosphere of molecular oxygen-containing gas or of an inert gas such as molecular nitrogen and carbon dioxide or of a mixture of the same, with a box-type dryer or a tunnel dryer which is generally used, specifically at a drying temperature of 100-350° C., preferably 130-300° C., more desirably 150-250° C., for 1-24 hours, preferably 2-20 hours, more desirably 3-16 hours.

In the calcination process, a conventional box-type oven or tunnel oven may be used with no particular limitation. Calcination temperature is 250-600° C., preferably 300-550° C., more desirably 350-450° C. Calcination time is 1-20 hours, preferably 2-10 hours. Calcination is conducted in an air atmosphere, an airflow, in an atmosphere of inert gas (e.g., molecular nitrogen or carbon dioxide), or in an inert gas flow.

Calcination is conducted after, or without, the above-mentioned secondary drying process. A supported body which has been made from catalytic precursor which had been prepared by the previous calcination of catalytically active components does not necessarily need to undergo a calcination process, but has only to pass through the above-mentioned secondary drying process so long as binder or adjuvant which might have been used in the supporting process can be removed.

Catalysts to be used in this invention which are different in pore size distribution in catalytically active component can be prepared by methods such as (1) a method of adjusting the ratio between ammonium ion and nitrate ion which are contained in the starting material mixture liquid, (2) a method of adjusting the drying condition (heating treatment in a gas stream with a box-type dryer, a tunnel dryer or the like) in the above-mentioned primary drying step, or (3) a method of adjusting the particle size of powdery catalytic precursor in the above-mentioned pulverizing process.

The above-mentioned method (1) of adjusting the ratio between ammonium ion and nitrate ion which are contained in the starting material mixture liquid comprises, fin example, changing the starting materials, or adding, to the starting material mixture liquid, a substance which contains nitrate ion or ammonium ion such as nitric acid, ammonia and ammonium nitrate. When the ratio of the number of moles of ammonium on to the number of moles of nitrate ion is 4 or higher, D1/D2 ratio is relatively small. If said ratio is less than 3, D1/D2 ratio is relatively large.

The above-mentioned method (2) of adjusting the drying condition in the primary drying step concretely comprises adjusting the ratio (V/W) of the amount V [L (standard state)/min.] of the atmospheric gas to be introduced into the dryer which has as concentration of molecular oxygen of 5-25%, to the mass W (kg) of the above-mentioned starting material mixture liquid or the mass W (kg) of the above-mentioned catalyst precursor such as cakey solid which has been prepared by the evaporation drying of starting material mixture liquid. For example, when the ratio (V/W) of the amount of molecular oxygen-containing gas as an atmospheric gas in the primary drying process to the mass of the starting material mixture liquid or the mass W of the cakey solid which has been prepared by the evaporation drying of starting material mixture liquid is adjusted to be at least 50, preferably at least 75, the ratio of D1/D2, D1 denoting the proportion of the total pore volume of pores whose pore diameter falls within the range of at least 0.03 µm and less than 0.4 µm to the total pore volume of the whole pores, and D2 denoting the proportion of the total pore volume of pores whose pore diameter falls within the range of at least 0.4 µm and at most 5 µm to the total pore volume of the whole pores, would be relatively small. When the ratio of V/W is adjusted to be less than 20, preferably less than 10, D1/D2 ratio would be relatively large.

In the above-mentioned method (3) of adjusting the particle size of powder of catalytic precursor in the pulverizing process, when the particle size of powder is less than 50 µm, preferably less than 20 µm, D1/D2 ratio would be relatively large. When said particle size is 100 µm or more, preferably 150 µm or more, D1/D2 ratio would be relatively small.

The above-mentioned methods (1), (2) and (3) for adjusting the pore size distribution in catalytically active component may be carried out either separately or in combination of two or three.

In this invention, there is no particular limitation on how to fill and arrange the catalyst, so long as each of reaction tubes of a fixed-bed multitubular reactor is filled with at least two species of catalysts which are different in the ratio of D1/D2, D1 denoting the proportion of the total pore volume of pores whose pore diameter falls within the range of at least 0.03 µm and less than 0.4 µm to the total pore volume of the whole pores, and D2 denoting the proportion of the total pore volume of pores whose pore diameter falls within the range of at least 0.4 µm and at most 5 µm to the total pore volume of the whole pores, in such a manner that layers (reaction zones) are formed axially in each of the reaction tubes.

In this invention, when each of reaction tubes of a fixed-bed multitubular reactor is filled, on the gas inlet side, with a catalyst which has a small D1/D2 ratio, and on the gas outlet side with a catalyst which has a large D1/D2 ratio, the yield of acrylic acid as the desired product improves as compared with the case where the D1/D2 ratio is constant. When, on the other hand, each of reaction tubes of a fixed-bed multitubular reactor is filled, on the gas inlet side, with a catalyst which has a large D1/D2 ratio, and on the gas outlet side with a catalyst which has a small D1/D2 ratio, catalyst life improves as compared with the case where the D1/D2 ratio is constant. This invention can thus improve either the yield of acrylic acid as the desired product or catalyst life, by arranging two or more catalysts which are different in D1/D2 ratio in reaction tubes.

In addition to the improvement in catalyst life, this invention achieves a very remarkable improvement in the yield of acrylic acid. In this respect, each of reaction tubes of a fixed-bed multitubular reactor is preferably filled, on the gas inlet side, with a catalyst which has a small D1/D2 ratio, and on the gas outlet side with a catalyst which has a large D1/D2 ratio.

In this invention. D1/D2 ratio is acceptably 0.1-5, preferably 0.2-4, more desirably 0.3-3.

There is also no particular limitation on the number of reaction zones. For industrial purpose, two or three reaction zones are enough to produce effects as desired. The dividing proportion of catalytic layer cannot be specified unconditionally since the optimum value is dependent on oxidation reaction conditions, or on the composition, shape or the size of catalyst with which to fill each layer. It would therefore be necessary to choose the dividing proportion appropriately so that optimal activity and selectivity may be attained as a whole.

When reaction tubes of a fixed-bed multitubular reactor are each filled with a catalyst in such a manner that three or more reaction zones are formed, it is not necessary to arrange the catalyst so that the D1/D2 ratio may increase progressively from the gas inlet side toward the gas outlet, or may decrease progressively from the gas inlet side toward the as outlet. Catalyst has only to be arranged so that, in at least two of the reaction zones, the pore size distribution of the filled catalyst satisfies the above-mentioned relationship. The objective of this invention is achieved also when the catalyst is arranged so that the D1/D2 ratio may firstly decrease and then increase, or firstly increase and then decrease, from the gas inlet side toward the gas outlet side.

This invention uses a fixed-bed multitubular reactor each of whose reaction tubes is filled with a catalyst for gas phase oxidation in the above-mentioned manner, for the purpose of the production of acrylic acid by catalytic gas phase oxidation of acrolein with molecular oxygen or a molecular oxygen-containing gas. Acrolein as a raw material for reaction includes not only purified acrolein but also acrolein-containing gas which is produced by the catalytic gas phase oxidation of propane and/or propylene or by the dehydration of glycerin.

The method of this invention is suitably applicable, for example, as a second stage of two-stage catalytic gas phase oxidation by which to produce acrylic acid from propylene as a starting material. In that case, an acrolein-containing gas which has been produced by the catalytic gas phase oxidation of propylene at the first stage may be used as it has been produced. It is, however, also acceptable to separate and purify acrolein, and add oxygen, water vapor or other gas to the same where necessary. There is no particular limitation placed on propylene as a raw material for the reaction at the first stage, examples of which include polymer grade propylene or chemical grade propylene, or propylene-containing mixed gas which is produced by the dehydrogenation or oxidative dehydrogenation of propane. This mixed gas may also contain air or oxygen where necessary.

There is no particular limitation on the reaction condition for the method of this invention; any reaction condition that has been generally employed in this type of reaction is usable. For example, a normal raw material gas for reaction (e.g., a mixed gas which comprises 1 to 15% by volume, preferably 4 to 12% by volume, of acrolein 0.5 to 25% by volume, preferably 2 to 20% by volume, of molecular oxygen, 0 to 30% by volume, preferably 0 to 25% by volume, of water vapor, and the balance of inert gas such as nitrogen) is suitably brought into contact with oxidation catalyst at a temperature ranging from 200 to 400° C., under a reaction pressure of 0.1 to 1.0 MPa, and at a space velocity of 300-5000 h$^{-1}$ (standard condition).

This invention is explained in detail by Examples below. The scope of this invention is, however, not to be limited by those Examples. In the following, "part(s) by mass" may be referred to as "part(s)" for the sake of simplicity Conversion and yield have been calculated in accordance with formulae below:

Conversion (mol %)=[(the number of moles of acrolein which has reacted)/(the number of moles of acrolein which has been fed)]×100

Selectivity (mol %)=[(the number of moles of acrylic acid which has been formed)/the number of moles of acrolein which has reacted)]×100

Yield (mol %)=[(the number of moles of acrylic acid which has been formed)/(the number of moles of acrolein which has been fed)]×100

Measurement of Pore Volume and Pore Size Distribution

The pore volume and pore size distribution of catalyst in this invention have been given as pore volume and pore size distribution per unit mass of catalyst, by measurement in a range of pore size from 0.003 to 200 μm with a mercury intrusion porosimeter (trademark: "AutoPore IV 9500", manufactured by Micromeritics Corporation), at an average pressure elevation rate of 0.005-0.3 MPa/sec.

Catalyst Production Example 1

Preparation of Catalyst (1)

To 2000 parts of deionized water which was being heated with stirring, 300 parts of ammonium paramolybdate, 91.1 parts of ammonium metavanadate and 26.8 parts of ammonium paratungstate were added to make a solution as chemical liquid (A). Separately, to 200 parts of deionized water which was being heated with stirring, 61.6 parts of copper nitrate, 49.5 parts of cobalt nitrate and 10.3 parts of antimony trioxide were added to give chemical liquid (B). Thus obtained two chemical liquids were mixed with each other to make a suspension. This suspension was dried with a spray dryer to give a solid matter. This solid matter was then pulverized to the size of 200 μm or less to give a powder of catalytic precursor. Rotary pan of a pan-type rolling granulator was charged firstly with α-alumina particles having an average particle diameter of 4.5 mm, and then with the above-mentioned powder of catalytic precursor while deionized water was being sprayed as a binder, and, thus, spheric, granules were formed. Thus obtained supported body was calcined at 400° C. for six hours in an air atmosphere to give catalyst (1). This catalyst (1) was composed of metallic elements, except for oxygen and carrier, as follows:

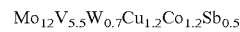

$Mo_{12}V_{5.5}W_{0.7}Cu_{1.2}Co_{1.2}Sb_{0.5}$

Calculation based on the following equation indicated that the carrying amount was 37% by mass.

Carrying amount (mass %)=[(mass of catalytically active components supported)/9(mass of inert carrier)]×100

Catalyst Production Example 2

Preparation of Catalyst (2)

Catalyst Production Example 1 was repeated except that the solid matter which had been produced by drying was pulverized to the size of 70 μm or less to give a catalytic precursor, and thus, catalyst (2) was obtained.

Catalyst Production Example 3

Preparation of Catalyst (3)

Catalyst Production Example 1 was repeated except that the powder of catalytic precursor was pulverized to the size of 10 μm or less, and, thus, catalyst (3) was obtained.

Catalyst Production Example 4

Preparation of Catalyst (4)

Catalyst Production Example 2 was repeated except that 145 parts of 25% by mass of ammonia water was added to chemical liquid (A), and, thus, catalyst (4) was obtained.

Catalyst Production Example 5

Preparation of Catalyst (5)

Catalyst Production Example 2 was repeated except that the suspension which had been obtained by the mixing of chemical liquid (A) and chemical liquid (B) with each other was dried by evaporation to give a solid matte's, and, thus, catalyst (5) was obtained.

Catalyst Production Example 6

Preparation of Catalyst (6)

Catalyst Production Example 2 was repeated except that the powder of catalytic precursor was dried at 180° C. for two hours, and, thus, catalyst (6) was obtained.

Table 1 shows how to prepare catalysts (1) to (6) and the pore volume of each of the same.

Comparative Examples 1 and 2

An acrolein-oxidizing reaction was conducted in the same manner as in Example 1 except that reaction tubes were each filled only with catalyst. (1) to make a layer length of 3000 mm (Comparative Example 1), or only with catalyst (2) to make a layer length of 3000 mm (Comparative Example 2). Results are shown in Table 2. As compared with Example 1, yield was low both when the initial 100 hours of oxidation reaction had passed, and when 4000 hours had passed, and the rate of reaction temperature elevation with time was large.

Comparative Example 3

An acrolein-oxidizing reaction was conducted in the same manner as in Example 1 except that reaction tubes were each filled firstly with catalyst (1) to make a layer length of 1500 mm and then with catalyst (4) to make a layer length of 1500 mm from the direction of reaction gas inlet side toward the outlet side. Catalyst (1) and catalyst (4) had the same value of D1/D2 ratio. As shown in Table 2, yield was low both when the initial 100 hours of oxidation reaction had passed, and when 4000 hours had passed, and the rate of reaction temperature elevation with, time was large, as compared with Example 1.

Example 2

An acrolein-oxidizing reaction was conducted in the same manner as in Example 1 except that reaction tubes were each filled, from the direction of reaction gas inlet side toward the outlet side, firstly with catalyst (1) to make a layer length of 1200 mm, subsequently with catalyst (2) to make a layer

TABLE 1

| Catalyst | Particle size of the powder of catalytic precursor pulverized | Drying method | Note | Carrying amount (mass %) | Pore volume (cc/g) | D1 (*1) | D2 (*2) | D1/D2 |
|---|---|---|---|---|---|---|---|---|
| (1) | 200 μm or less | Spray-dried | | 37 | 0.165 | 30 | 52 | 0.59 |
| (2) | 70 μm or less | Spray-dried | | 37 | 0.145 | 41 | 48 | 0.86 |
| (3) | 10 μm or less | Spray-dried | | 38 | 0.141 | 46 | 43 | 1.08 |
| (4) | 70 μm or less | Spray-dried | Ammonia was added. | 37 | 0.180 | 33 | 56 | 0.59 |
| (5) | 70 μm or less | Evaporation-dried | | 38 | 0.160 | 25 | 63 | 0.40 |
| (6) | 70 μm or less | Spray-dried | Dried at 180° C. for 2 Hr. | 36 | 0.155 | 52 | 39 | 1.33 |

*1 The proportion (%) of the total pore volume of pores whose pore diameter falls within the range of at least 0.03 μm and less than 0.4 μm to the total pore volume of the whole pores.
*2 The proportion of the total pore volume of pores whose pore diameter falls within the range of at least 0.4 μm and at most 5.0 μm to the total pore volume of the whole pores.

Example 1

A reactor which comprised 24 steel-made reaction tubes, each having an inner diameter of 25 mm, which were covered with a shell in which to flow a heating medium was charged firstly with catalyst (1) to make a layer length of 1500 mm and then with catalyst (2) to make a layer length of 1500 mm, from the direction of reaction gas inlet side toward the outlet side. A gas mixture which, comprised 4.5% by volume of acrolein, 5.5% by volume of oxygen, 18% by volume of water vapor and 72% by volume of nitrogen was introduced at a space velocity of 2000 h$^{-1}$ (standard state), and, thus, an acrolein-oxidizing reaction was continued for a reaction time of 4000 hours while reaction temperature which was initially 260° C. was changed suitably so that the conversion of acrolein might be about 98.5%. Results are shown in Table 2.

length of 1000 mm, and further with catalyst (3) to make a layer length of 800 mm. Results are shown in Table 2.

Example 3

An acrolein-oxidizing reaction was conducted in the same manner as in Example 1 except that reaction tubes were each filled, from the direction of reaction gas inlet side toward the outlet side, firstly with catalyst (5) to make a layer length of 1500 mm, subsequently with catalyst (6) to make a layer length of 1500 mm. Results are shown in Table 2.

Comparative Examples 4 and 5

An acrolein-oxidizing reaction was conducted in the same manner as in Example 3 except that reaction tubes were each filled only with catalyst (5) to make a layer length of 3000 mm (Comparative Example 4), or only with catalyst. (6) to make a layer length of 3000 mm (Comparative Example 5). Results are shown in Table 2. As compared with Example 3, yield was low both when the initial 100 hours of oxidation reaction had passed, and when 4000 hours had passed.

Example 4

An acrolein-oxidizing reaction was conducted in the same manner as in Example 1 except that reaction tubes were each filled, from the direction of reaction gas inlet side toward the outlet side, firstly with catalyst (3) to make a layer length of 1000 mm, and subsequently with catalyst (1) to make a layer length of 2000 mm. Results are shown in Table 2.

Example 5

An acrolein-oxidizing reaction was conducted in the same manner as in Example 1 except that reaction tubes were each filled, from the direction of reaction gas inlet side toward the outlet side, firstly with catalyst (4) to make a layer length of 1500 mm, subsequently with catalyst. (2) to make a layer length of 1000 mm, and further with catalyst (1) to make a layer length of 500 mm. Results are shown in Table 2.

Example 6

An acrolein-oxidizing reaction was conducted in the same manner as in Example 1 except that reaction tubes were each filled, from the direction of reaction gas inlet side toward the outlet side, firstly with catalyst (3) to make a layer length of 800 mm, subsequently with catalyst (1) to make a layer length of 1000 m, and further with catalyst (2) to make a layer length of 1200 mm. Results are shown in Table 2.

TABLE 2

| | Catalysts filled Gas inlet side → Gas outlet side (D1/D2) | Reaction Time (Hr) | Reaction temperature (° C.) | Conversion of acrolein (mol %) | Selectivity of acrylic acid (mol %) | Yield of acrylic acid (mol %) |
|---|---|---|---|---|---|---|
| Example 1 | Catalyst (1) / Catalyst (2) | 100 | 261 | 98.5 | 95.5 | 94.1 |
| | 1500 mm / 1500 mm | 4000 | 265 | 98.6 | 95.6 | 94.3 |
| | (0.59 / 0.86) | | | | | |
| Comparative Example 1 | Catalyst (1) | 100 | 263 | 98.4 | 95.2 | 93.7 |
| | 3000 mm | 4000 | 269 | 98.5 | 95.1 | 93.7 |
| | (0.59) | | | | | |
| Comparative Example 2 | Catalyst (2) | 100 | 261 | 98.5 | 95.1 | 93.7 |
| | 3000 mm | 4000 | 267 | 98.5 | 95.1 | 93.7 |
| | (0.86) | | | | | |
| Comparative Example 3 | Catalyst (1) / Catalyst (4) | 100 | 264 | 98.4 | 95.0 | 93.5 |
| | 1500 mm / 1500 mm | 4000 | 271 | 98.5 | 95.0 | 93.6 |
| | (0.59 / 0.59) | | | | | |
| Example 2 | Catalyst (1) / Catalyst (2) / Catalyst (3) | 100 | 260 | 98.6 | 95.6 | 94.3 |
| | 1200 mm / 1000 mm / 800 mm | 4000 | 264 | 98.6 | 95.7 | 94.4 |
| | (0.59 / 0.86 / 1.08) | | | | | |
| Example 3 | Catalyst (5) / Catalyst (6) | 100 | 260 | 98.5 | 95.6 | 94.2 |
| | 1500 mm / 1500 mm | 4000 | 264 | 98.5 | 95.6 | 94.2 |
| | (0.40 / 1.33) | | | | | |
| Comparative Example 4 | Catalyst (5) | 100 | 262 | 98.5 | 95.2 | 93.8 |
| | 3000 mm | 4000 | 271 | 98.5 | 95.1 | 93.7 |
| | (0.40) | | | | | |
| Comparative Example 5 | Catalyst (6) | 100 | 260 | 98.5 | 95.0 | 93.6 |
| | 3000 mm | 4000 | 266 | 98.6 | 95.0 | 93.7 |
| | (1.33) | | | | | |
| Example 4 | Catalyst (3) / Catalyst (1) | 100 | 263 | 98.5 | 95.3 | 93.9 |
| | 1000 mm / 2000 mm | 4000 | 265 | 98.4 | 95.4 | 93.9 |
| | (1.08 / 0.59) | | | | | |
| Example 5 | Catalyst (4) / Catalyst (2) / Catalyst (1) | 100 | 263 | 98.5 | 95.4 | 94.0 |
| | 1500 mm / 1000 mm / 500 mm | 4000 | 268 | 98.5 | 95.3 | 93.9 |
| | (0.59 / 0.86 / 0.59) | | | | | |
| Example 6 | Catalyst (3) / Catalyst (1) / Catalyst (2) | 100 | 263 | 98.5 | 95.4 | 94.0 |
| | 800 mm / 1000 mm / 1200 mm | 4000 | 266 | 98.6 | 95.4 | 94.1 |
| | (1.08 / 0.59 / 0.86) | | | | | |

The invention claimed is:

1. A method for producing acrylic acid by the catalytic gas-phase oxidation of acrolein with molecular oxygen or molecular oxygen-containing gas by a fixed-bed multitubular reactor which has been filled with catalyst, which method comprises filling each of reaction tubes of a fixed-bed multitubular reactor with at least two species of catalysts each of which essentially comprises, as catalytically active components, oxide of molybdenum and oxide of vanadium and/or composite oxide of the same, said at least two species of catalysts being different in the ratio of D1/D2, D1 denoting the proportion of the total pore volume of pores whose pore diameter falls within the range of at least 0.03 μm and less than 0.4 μm to the total pore volume of the whole pores, and D2 denoting the proportion of the total pore volume of pores whose pore diameter falls within the range of at least 0.4 μm and at most 5 μm to the total pore volume of the whole pores, in such a manner that at least two reaction zones are formed axially in each of the reaction tubes.

2. The method of claim 1 for producing acrylic acid wherein said catalyst comprises a catalytically active component of formula (1) as follows:

$$Mo_{12}V_aW_bA_cB_dC_eD_fO_x \qquad (1)$$

wherein Mo is molybdenum; V is vanadium; W is tungsten; A is at least one species of element selected from the group consisting of chromium, manganese, iron, cobalt, nickel, copper, zinc and bismuth; B is at least one species of element selected from the group consisting of antimony, niobium, tin, tellurium and phosphorus; C is at least one species of element selected from the group consisting of silicon, aluminum, titanium, cerium and zirconium; D is at least one species of element selected from the group consisting of alkali metals and alkaline earth metals; and O is oxygen; and a, b, c, d, e, f and x each denote number of atoms of V, W, A, B, C, D and O, and $0<a \leq 14$, $0 \leq b \leq 12$, $0 \leq c \leq 30$, $0 \leq d \leq 6$, $0 \leq e \leq 50$, and $0 \leq f \leq 6$, and x is a value determined by the state of oxidation of each of the elements.

3. The method of claim 1 for producing acrylic acid wherein said catalyst is a supported catalyst in which the above-mentioned catalytically active component is supported on an inert carrier of a specific shape.

4. The method of claim 1 for producing acrylic acid wherein each of reaction tubes of a fixed-bed multitubular reactor is filled, on the gas inlet side, with a catalyst which has a small D1/D2 ratio, and on the gas outlet side with a catalyst which has a large D1/D2 ratio.

5. The method of claim 1 for producing acrylic acid wherein D1/D2 ratio is 0.1 to 5.

6. The method of claim 2 for producing acrylic acid wherein said catalyst is a supported catalyst in which the above-mentioned catalytically active component is supported on an inert carrier of a specific shape.

7. The method of claim 2 for producing acrylic acid wherein each of reaction tubes of a fixed-bed multitubular reactor is filled, on the gas inlet side, with a catalyst which has a small D1/D2 ratio, and on the gas outlet side with a catalyst which has a large D1/D2 ratio.

8. The method of claim 3 for producing acrylic acid wherein each of reaction tubes of a fixed-bed multitubular reactor is filled, on the gas inlet side, with a catalyst which has a small D1/D2 ratio, and on the gas outlet side with a catalyst which has a large D1/D2 ratio.

9. The method of claim 2 for producing acrylic acid wherein D1/D2 ratio is 0.1 to 5.

10. The method of claim 3 for producing acrylic acid wherein D1/D2 ratio is 0.1 to 5.

11. The method of claim 4 for producing acrylic acid wherein D1/D2 ratio is 0.1 to 5.

* * * * *